(12) United States Patent
Apple et al.

(10) Patent No.: US 7,029,431 B2
(45) Date of Patent: Apr. 18, 2006

(54) DIRECTIONAL-IONIZING ENERGY EMITTING IMPLANT

(76) Inventors: Melvin J. Apple, 2553 NW. 52nd St., Boca Raton, FL (US) 33496; Marc G. Apple, 1606 Sycamore Hills Dr., Fort Wayne, IN (US) 46804

( * ) Notice: Subject to any disclaimer, the term of this patent is extended or adjusted under 35 U.S.C. 154(b) by 0 days.

(21) Appl. No.: 10/421,032

(22) Filed: Apr. 24, 2003

(65) Prior Publication Data

US 2004/0215047 A1    Oct. 28, 2004

(51) Int. Cl.
*A61N 5/00*    (2006.01)
(52) U.S. Cl. .......................................................... 600/3
(58) Field of Classification Search ............... 623/1.34, 623/32; 600/1–8; 606/2, 21, 27; 607/88, 607/89, 96, 100, 101, 113
See application file for complete search history.

(56) References Cited

U.S. PATENT DOCUMENTS

| | | | |
|---|---|---|---|
| 4,754,745 A * | 7/1988 | Horowitz ........................ | 600/8 |
| 6,010,445 A * | 1/2000 | Armini et al. .................. | 600/3 |
| 6,030,333 A * | 2/2000 | Sioshansi et al. ............... | 600/3 |
| 6,143,431 A * | 11/2000 | Webster ........................ | 428/669 |
| 6,264,599 B1 * | 7/2001 | Slater et al. .................... | 600/7 |
| 6,293,899 B1 * | 9/2001 | Sioshansi et al. ............... | 600/3 |
| 6,394,945 B1 * | 5/2002 | Chan et al. ..................... | 600/3 |

\* cited by examiner

*Primary Examiner*—Samuel G. Gilbert
(74) *Attorney, Agent, or Firm*—Taylor & Aust, P.C.

(57) ABSTRACT

The directional-ionizing energy emitting implant is for attachment either to natural tissue or a prosthetic device, and delivers a prescribed dosage of energy to targeted tissue. The insert device includes an energy-source material within the insert device that delivers the prescribed dosage of energy to the targeted tissue, while minimizing exposure of nontargeted tissue. The targeted tissue has a known energy-response profile and is adjacent to the targeted tissue. The energy-source material in combination with the prosthetic device defines an actual energy-delivery distribution field. The energy-delivery distribution field has a configuration similar to the known energy-responsive profile of the targeted tissue. The prescribed dosage of energy is applied from energy-source material within the insert device and directed to the targeted tissue. The prescribed energy dosage is determined by using known characteristics of the energy-source material, and by the placement of the energy-source material relative to the targeted tissue. The implant system reduces any occurrence of heterotopic ossification caused by the implant, inhibits growth or migration of benign or malignant living cells, and minimizes or even eliminates infectious processes or delayed keloid or scar formation induced from surgical placement of a functional prosthesis or fixation device, in tissue within or about the device due to its targeted therapeutic energy emission effects.

4 Claims, 4 Drawing Sheets

DIRECTIONAL-IONIZING ENERGY EMITTING IMPLANT

FIELD OF USE

The present invention relates to an implanted apparatus having an insert device that is additive to or the replacement for an anatomic body structure or joint for the purpose of delivering a prescribed dosage of energy to targeted tissue to inhibit growth or migration of benign or malignant living cells and to minimize or even eliminate infectious or inflammatory processes, scarring, and fibrosis in tissue within or about the device due to its targeted energy effects.

BACKGROUND OF THE INVENTION

Total or partial prosthetic replacements are now common orthopedic surgical procedures. As the age of the general population increases, the number of such replacements is also increasing. Common symptoms generally can be caused by progressive degenerative osteoarthritis, prior localized trauma, previous local surgical procedures within the region, ankylosing spondylitis, and idiopathic skeletal hyperostosis.

A common delayed complication following such replacements is the development of heterotopic ossification within or about the adjacent soft tissue and the prosthesis between the adjoining bone tissue. This complication results from excessive migration, replication, or differentiation of local primitive mesenchymal cells which are stimulated by the surgical trauma. These cells undergo subsequent metabolic and cytologic metamorphosis to become more specialized osteoblastic cells. These osteoblastic cells then produce osteoid which is eventually transformed into calcified deposits or bone tissue, but in undesirable locations.

Heterotopic ossification causes varying degrees of debilitating pain, functional or mobile impairment, and increases the likelihood of repeat procedures after a period of time from several months to a few years. Between 30 and 35 percent of all untreated patients undergoing total hip prosthesis develop some degree of functional impairment or progressive discomfort, often from heterotopic ossification.

It has been shown in our U.S. Pat. No. 6,120,540 that a radio prosthesis comprising a prosthetic device and a radio source material that is part of the prosthesis device has utility, for example, in a total hip replacement. The radio prosthesis is precalibrated to deliver for dosage, dose rate, and depth dose to adjacent target tissue to inhibit growth. Such radiation begins its effective delivery immediately at the time of the procedure and over the immediate critical time frame for heterotopic ossification formation. Since the radiation only travels a short distance to the targeted area, there is minimal exposure of radiation to medical personnel and healthy tissue within the patient. The dosage eventually decays to a non-radioactive state thereby enabling healing without functional impairment to the prosthesis. No separate removal procedure is required. The patient is discharged upon recovery and receives the equivalent radiation benefit of several fractionated external beam treatments without the time, inconvenience, discomfort, and expense of conventional radio therapy.

External beam irradiation has established therapeutic effectiveness. When such therapy is delivered within a narrow period of time, the prophylactic use of external beam radiation therapy has been shown to effectively reduce the incidence and severity of heterotopic ossification. A limited, relatively low-dose of focal ionizing radiation to the specific target tissue, when administered predominantly in the first several hours to two days after surgery has proven beneficial clinical results with virtually no side effects.

Other relevant art includes the following:

U.S. Pat. No. 5,681,289 (Wilcox et al) is a system for dispensing a liquid chemical agent, such as an antibiotic, anesthetic, growth factor, hormone, anti-neoplastic agent into a site of a surgical procedure. The system includes at least one bladder with an internal cavity that connects to an open tube through which the liquid chemical agent is passed, under pressure, into the bladder. The bladder is shaped to fit between a prepared bone section and a prosthesis. The bladder is connected by a tube to a reservoir and pump.

U.S. Pat. No. 4,936,823 (Colvin et al) is an implant capsule for insertion into a body canal of a patient to apply radiation treatment to a selected portion of the body canal. The transendoscopic implant capsule is transported through the body canal to apply a therapeutic radiation to a tumor within the patient. The implant capsule is remotely implanted and retrieved with a fiber optic bronchoscope.

U.S. Pat. No. 5,833,593 (Liprie) is a flexible wire for providing a radioactive source to maneuver through a tortuous narrow passage to a treatment site within the patient. The source wire includes an elongated flexible housing tube with a treatment end modified to receive a radioactive core.

While U.S. Pat. No. 5,728,136 (Thal) discloses a spike member for insertion into a bone mass, we are unaware of any such device being used to delivery energy treatment to targeted tissue. External beam radiation therapy is often not prescribed because of the time required for set-up and treatment, the availability of single fraction treatments and variations in prescribed dose, patient discomfort and side effects, the need to irradiate tissue outside the target field, and economic considerations. In addition, many patients are not considered for radiation treatment until late in the recovery process, which further limits treatment options.

What is needed is a process and structure for providing the radiation dose originating from an internal site to the targeted tissue, whereby the emission profile more closely matches the profile of the targeted tissue; a process and a structure that can be readily adapted for any surgical bone tissue replacement or additive procedures; a process and a structure that is easy to administer, safe for the patient, effectively reducing side effects caused by such surgical procedures; and, a process and structure for eliminating the need for separate post-operative treatment while dramatically (a) reducing any occurrence of heterotopic ossification, and (b) minimizing infectious processes in tissue within or about the device and excessive, restriction fibroid and scarring at the incision or closure site due to its targeted radiation effects.

SUMMARY OF THE INVENTION

The needs set forth above are addressed by the directional-ionizing energy emitting implant system and process of the present invention. While the implant system of the present invention is discussed herein in relationship to the delivery of radiation to targeted tissue, one having ordinary skill in the art will readily appreciate the application of the principles of the present invention to other forms of ionizing energy delivery, including but not limited to luminescent energy, hyperthermic energy, and photo-light energy emission forms.

External beam irradiation establishes therapeutic effectiveness. The directional-ionizing energy emitting implant device of the present invention is for attachment either to natural tissue or a prosthetic device, and delivers a prescribed dosage of energy to targeted tissue. The implant device includes an energy-source material that delivers the prescribed dosage of energy to the targeted tissue, while minimizing exposure of nontargeted tissue. The targeted tissue has a known profile and is adjacent to the targeted tissue. The energy-source material in combination with the prosthetic device defines an actual energy-delivery distribution field. The energy-delivery distribution field has a configuration similar to the known profile of the targeted tissue. The prescribed dosage of energy is applied from energy-source material within the insert device and directed to the targeted tissue. The prescribed energy dosage is determined by using known characteristics of the energy-source material, and by the placement of the energy-source material relative to the targeted tissue. The implant system reduces the occurrence of heterotopic ossification caused by the implant, inhibits growth or migration of benign or malignant living cells, and minimizes or even eliminates infectious processes or delayed keloid or scar formation induced from surgical placement of a functional prosthesis or fixation device, in tissue within or about the device due to its targeted radiation effects.

The present invention is a directional-ionizing energy emitting implant device and a method for delivering a dosage of radiation to targeted tissue. The system comprises a prosthetic device that functionally replaces or is additive to a body structure or joint, and radio source material. The radio source material is positioned either on or within the prosthetic device. The actual radiation delivery distribution field has a similar configuration to the profile of the targeted tissue. The implant system is particularly useful to minimize or even eliminate infectious or inflammatory processes or delayed keloid or scar formation induced from surgical placement of a functional prosthesis or fixation device in tissue within or about the device due to its targeted radiation effects.

When such therapy is delivered within a narrow period of time, the prophylactic use of external beam radiation therapy demonstrates an effective reduction of the incidence and severity of heterotopic ossification. A limited, relatively low-dose of focal ionizing radiation to the specific target tissue, when administered predominantly in the first several hours to two days after surgery has proven beneficial clinical results with virtually no short or long term side effects.

Additional indications for the use of localized, relatively modest, cumulative radiation doses of approximately 600 cGY to 3500 cGy, have demonstrated clinical success in providing some bacteriocidal, bacteriostatic, and sterilizing benefits for living tissue. In addition, similar dose applications inhibit keloid excess scar formation. Such keloid formation at the skin or sub-dermal tissue within or about a surgical scar or injury can cause significant restriction of motion, dys-mobility, pain, or decreased aesthetic appearance.

Ionizing-type radiation exposure is also routinely used in various ways to sterilize and leukocytic reduce blood products from infectious and immunoreactive agents in dose ranges of 1500 to 2500 cGy or more, depending upon the method of fractionation and dose rate and type of energy administration.

The directional-ionizing energy emitting implant device and method of the present invention offer numerous medical, safety and economic advantages over conventional radiotherapy. The structure of this system dramatically improves the delivery of the radiation to the targeted tissue as compared with the non-targeted tissue, inherently accommodating for individual patient differences in morphology. Improved radiation efficacy is achieved by delivering a continuous dose rate of radiation and by utilizing known characteristics of various radio nuclides; such as half-life, specific activity, specific concentration, and type of energy decay.

The artificially implanted apparatus is functionally replacing or is additive to a normal anatomic body structure or joint. The apparatus is implanted, imbedded, or contained in a housing for strategically localized solid, liquid, gel-like, gaseous, or other intermediate phase radio-emitting substance or capable of inducing ionizing radiation, phosphorescence, luminescence, or fluorescence; whereby a precalibrated general or specific total dose, dose rate, or depth dose is delivered to adjacent target tissue to inhibit growth, migration, or differentiation of benign or malignant living cells; to inhibit heterotopic ossification; and to minimize infectious or inflammatory processes or minimize delayed scar or keloid formation in such tissue.

Since the radiation only travels a short distance within the patient's soft tissue and essentially only through the targeted area, there is minimal radiation risk to medical personnel and healthy tissue within the patient. Such radiation may begin its effective delivery immediately at the time of the procedure or is activated in delay post-operatively and over the immediate critical time frame for heterotopic ossification formation and/or minimize infectious, inflammatory, or scarring processes in such tissue. The radio nuclide dosage eventually decays to a non-radioactive state thereby enabling healing and without functional impairment to the prosthesis or fixation devices. The patient is discharged after recovery and receives the equivalent radiation benefit of several fractionated external beam treatments without the time, inconvenience, discomfort, and expense of conventional radiotherapy, while minimizing exposure to nontargeted tissue. Also, the system and method of the present invention promote more routine use of prophylactic radiation to prevent heterotopic ossification and minimize infectious, inflammatory, or scarring processes in such tissue by enabling potential broader physician access, flexible treatment judgments, and less patient pain and inconvenience.

While the directional-ionizing energy emitting implant system of the present invention is discussed herein in relationship to hip-joint, it is to be appreciated by one having ordinary skill in the art that this technology is also applicable to total or partial joint replacement, and injury or fracture fixation, such as a total or partial hip, knee, shoulder, or elbow prosthesis. For purposes of discussion herein, unless the context suggests otherwise, a hip replacement is used for purpose of illustration only. The radiation delivery system of the present invention induces the emission of specific radio nuclides enabling the anatomic configuration of the implant, the controlled placement position of one or more radio nuclides, and the selection of the type or composition of the radio source material to deliver a confined and targeted tissue deposition of ionizing radiation to a pre-calibrated dose rate, depth dose, and total delivered dose of prescribed radiation.

For a more complete understanding of the directional-ionizing energy-emitting implant of the present invention, reference is made to the following detailed description and accompanying drawings in which the presently preferred embodiments of the present invention are shown by way of example. As the invention may be embodied in many forms

MODES FOR CARRYING OUT THE INVENTION

The implant of the present invention is useful in applications involving the replacement or addition of bone tissue. The radiation delivery system induces the emission of specific radio nuclides enabling the anatomic configuration of the implant, the controlled placement position of one or more radio nuclides, and the selection of the type or composition of the radio source material to deliver a confined and targeted tissue deposition of ionizing radiation to a pre-calibrated dose rate, depth dose, and total delivered dose of prescribed radiation.

Figure 1:
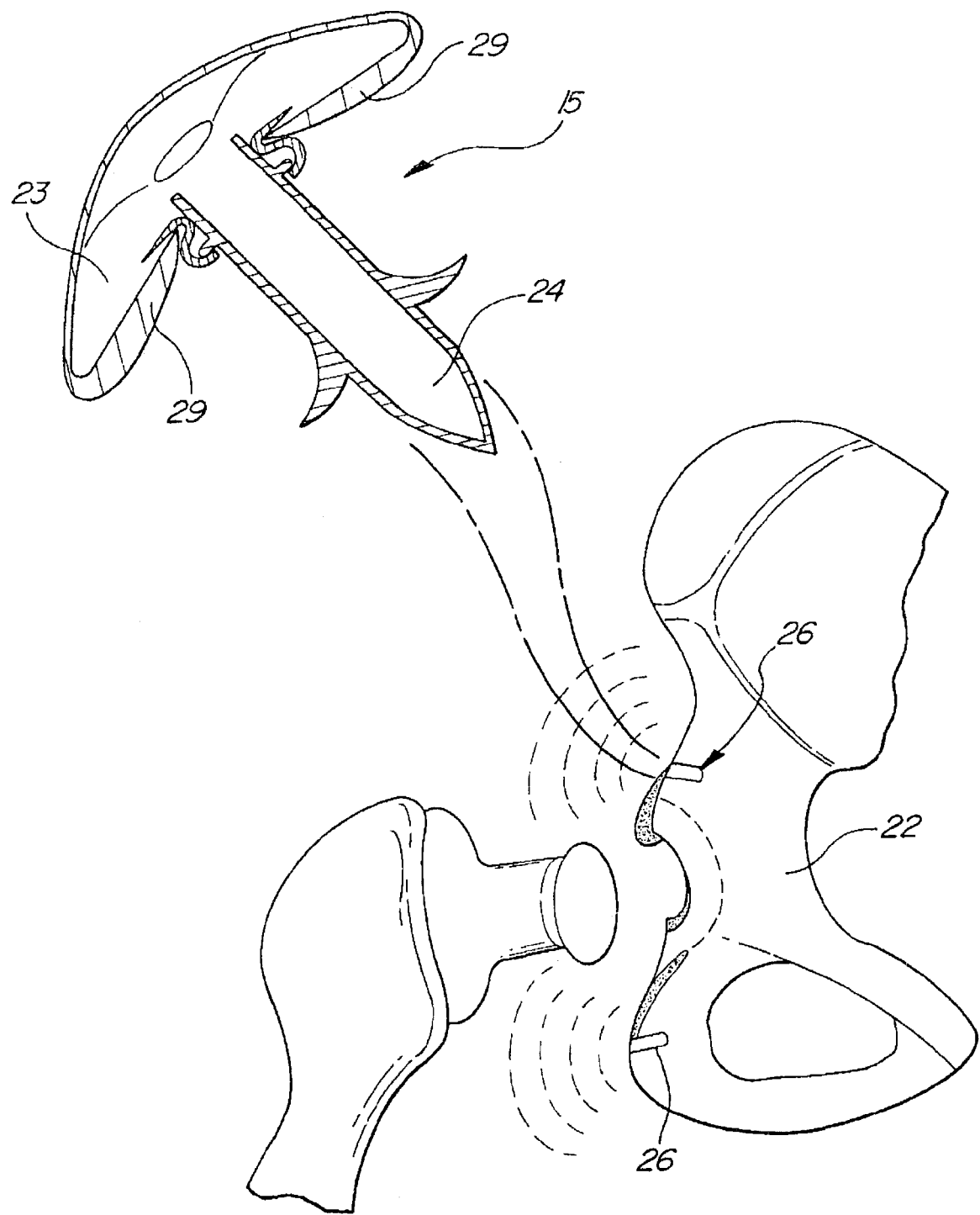
FIG. 1 is an assembly view of a first preferred embodiment of a directional-ionizing energy emitting implant device of the present invention, the implant device being a spike for placement into a hip joint, the view of the spike being enlarged relative to the hip joint, the hip joint including a bone fixation port for receiving and securing the spike, the spike including a detachable cap, radio nuclide materials under the cap, the cap member being detachable once surgically placed within the hip joint.

Referring now to the drawings, FIG. 1 is an assembly view of a first preferred embodiment of a implant or insert member [15] of the present invention, the insert member [15] being a spike or insert member [15] for placement into a hip joint [22], the view of the spike or insert member [15] being enlarged relative to the hip joint [22], the hip joint [22] including a bone fixation port [26] for receiving and securing the spike or insert member [15], the spike or insert member [15] including a detachable cap portion [23], radio nuclide materials under the cap portion [23], the cap portion [23] member being detachable once surgically placed within the hip joint [22].

The insert member [15] is for attachment either to organic tissue or a prosthesic device [20], and delivers a prescribed dosage of radiation to targeted tissue. The insert member [15] includes an radio source material within the insert member [15] delivers the prescribed dosage of radiation to the targeted tissue, while minimizing exposure of nontargeted tissue. The targeted tissue has a known radio response and sensitivity profile and is adjacent to the targeted tissue. The radio-source material in combination with the prosthesic device [20] defines an actual radiation-delivery distribution field. The radiation-delivery distribution field has a configuration similar to the known radio response and sensitivity profile of the targeted tissue. The prescribed dosage of radiation is applied from radio-source material within the insert member [15] and directed to the targeted tissue. The prescribed radiation dosage is determined by using known characteristics of the radio-source material, and by the placement of the radio-source material relative to the targeted tissue. The implant system reduces the occurrence of heterotopic ossification caused by the implant, inhibits growth or migration of benign or malignant living cells, and minimizes or even eliminates infectious and inflammatory processes or delayed keloid or scar formation induced from surgical placement of a functional prosthesis or fixation device, in tissue within or about insert member [15] due to its targeted radiation effects.

The radio nuclide materials include but are not limited to solids, particles, gels, liquids, or gas radio nuclide materials for therapy. The insert member [15] comprises a cap portion [23] and an elongated portion [24]. The cap portion [23] of the insert may either be detachable or integral with the insert member [15]. The elongated portion [24] projects into and locks into bone tissue or prosthesic device [20]. The insert member [15] may also be an anchor, a plate, a screw or other device that is attachable to organic tissue—such as bone, cartilage, or the like. The insert member [15] may also be secured to a prosthesic device [20].

Extending outward from the elongated portion [24] of the insert member [15] is a projection. The projection is preferably made of titanium or other alloy metal. The projection is initially closed and becomes engaged once inserted into the bone tissue. The bone tissue includes a bone-fixation port [26], the port [26] being drilled or nailed to a depth of a few millimeters to centimeters. The bone ports [26] used for spike or insert member [15] retention may be activated outward from a disengaged, internal position from the cap portion [23] of the insert member [15], or from an internally placed energy-emitting component that is placed and locked.

The radio nuclide material is preferably loaded into the cap portion [23] of the insert member [15] prior to implant, but may also be loaded after implant is completed. The radio nuclide material may be either integral with the cap portion [23] or attachable therewith. In one preferred embodiment, the emitting radio-seed, radio-wire, or radio-pellets are placed into the cap portion [23] of the insert member [15] prior to implant. Disposed on the undersurface of the cap portion [23] is a bone surface "attenuating" shield component. This shield [29] is designed to minimize expose of nontargeted tissue.

Directional emission of energy to the target tissue is provided by the external shape of the insert member [15], the type of materials employed.

Figure 2:
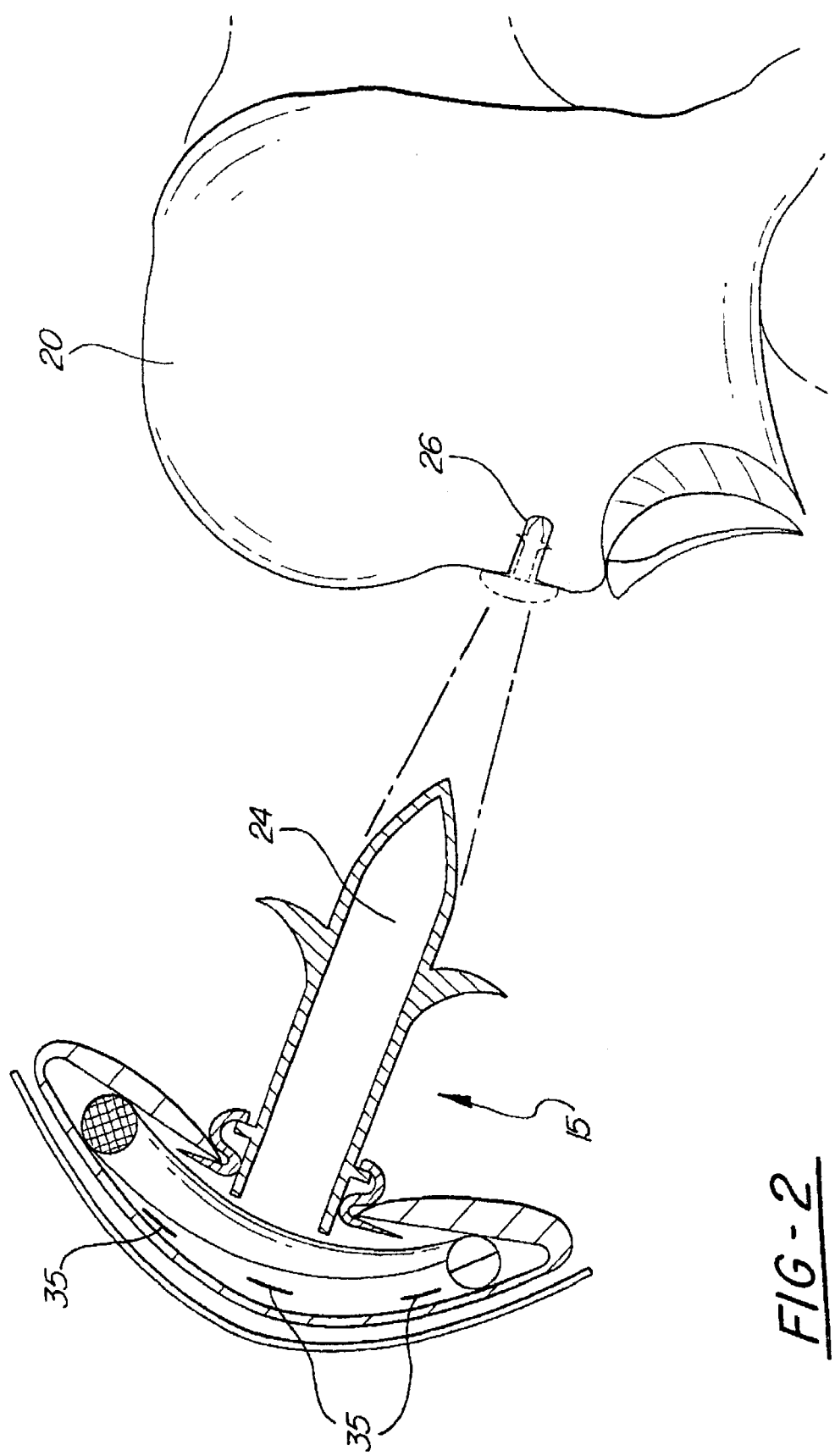
FIG. 2 is an assembly view of a second preferred embodiment of the directional-ionizing energy emitting implant device of the present invention for retention relative to a hip joint, the implant device being enlarged relative to the hip joint, the insert member including an engageable locking clasp to secure the insert member relative to the hip joint once implanted.

FIG. 2 is an assembly view of a second preferred embodiment of the directional-ionizing energy emitting implant or insert member [15] of the present invention for retention relative to a hip joint [22], the insert member [15] being enlarged relative to the hip joint [22], and the insert member [15] including an engageable locking clasp to secure the insert member [15] relative to the hip joint once implanted.

The top surface of the insert member [15] is preferable a removable radio-protection tape or covering. Disposed within a fixed or attachable top of the cap portion [23] of the insert member [15] are radio nuclide channels, pockets, or reservoirs. Also, disposed in the cap portion [23] of the insert member [15] is an injectable or external access port [26] to place the radio nuclide materials. The top of insert member [15] abuts the outer surface of the bone tissue. The depth placement canals in the bone ports [26] are preferably drilled to a depth of between 5 and 15 mm.

Disposed on the undersurface of the cap portion [23] of the insert member [15] is a radio-attenuating shield [29] or a magnetized element to shift radio-emision of the charged particles. A plurality of engageable, locking clasps are disposed proximate to the cap portion [23] on the elongated portion [24] of the insert member [15].

Underneath the removable top of the cap portion [23] of the insert member [15] portion are disposed positionally placed radio-opaque markers. Localization matching of the cap portion [23] of the insert member [15] enable alignment, and may comprise markings [35] in the form of labels, demarcations, symbols, that are positionable to prosthesis [20] or insert member [15]. The alignment markers are disposed proximate to a partial or complete acetabular joint prosthesis [20]. The alignment markers are useful for verifying positioning and alignment.

Figure 3:
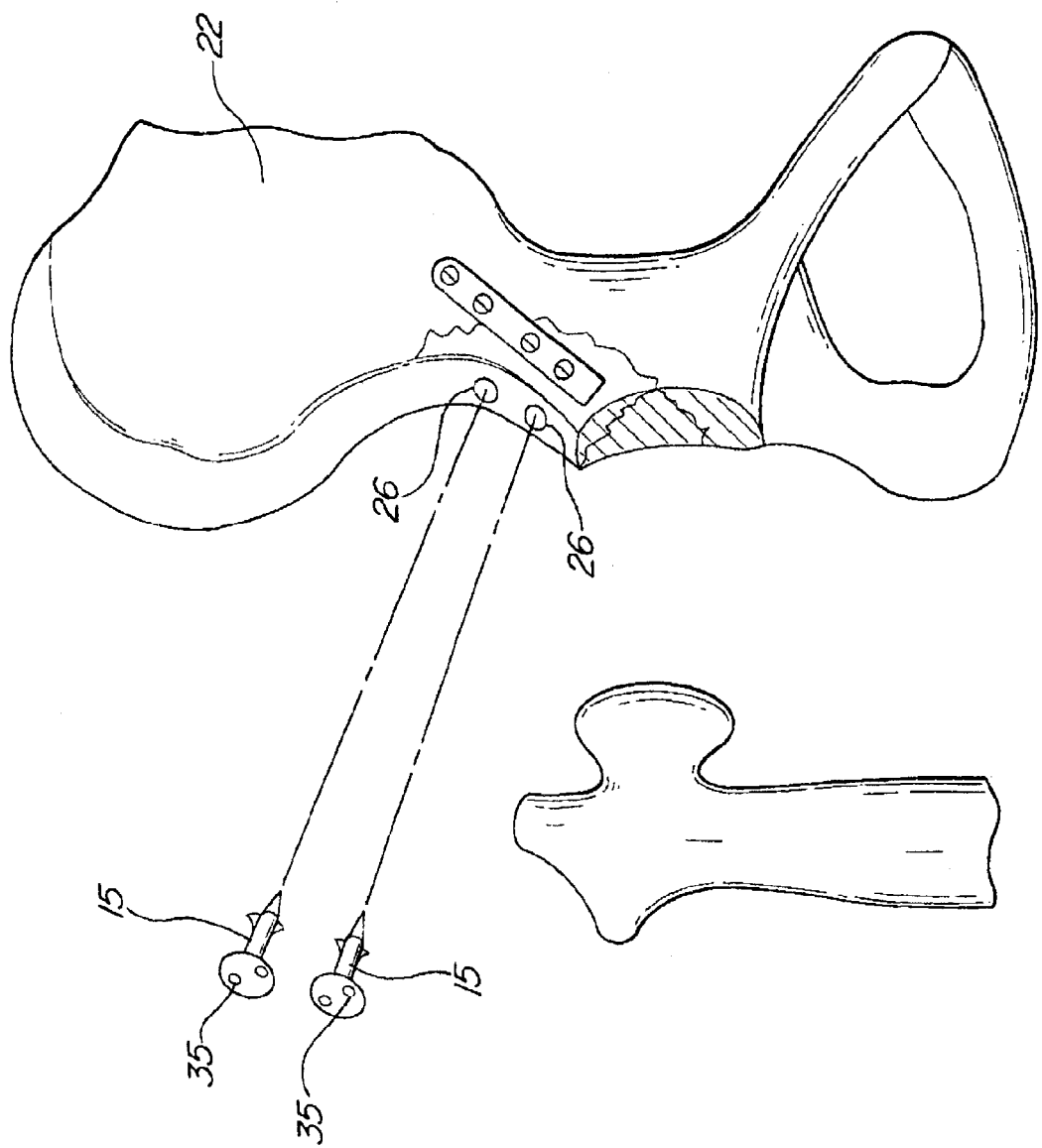
FIG. 3 is an assembly view of a third preferred embodiment of a pair of directional-ionizing energy emitting implant devices of the present invention for retention into a hip joint, the hip joint including a fixation plate for stabilizing the fractured hip joint, the hip joint including ports for accepting the pair of implant devices, the implant devices having externally identifiable demarcations necessary to properly provide distance, orientation, and alignment.

FIG. 3 is an assembly view of a third preferred embodiment of a pair of directional-ionizing energy emitting implants or insert members [15] of the present invention for retention into a hip joint, the hip joint including ports [26] for accepting the pair of insert members [15], the insert members [15] having externally identifiable demarcations or markings [35] necessary to properly provide distance, orientation, and alignment.

Externally identifiable demarcations or markings [35] that are either visible, palpable, or measurable are disposed on the insert member [15] to enable distance, orientation, and alignment for placement of the insert member [15] in the bone tissue, in relationship to the plates or prosthesis [20], in order to deliver accurate, directional-ionizing energy emissions or activation.

The hip joint [22] includes a fixation plate secured to the hip-joint for stabilizing the fractured hip joint. The fixation plate includes four fasteners. The insert members [15] are retained within spatially, accurately placed radio module ports [26] within the hip.

In another preferred embodiment of the implant device of the present invention, the identifiable markings [35] are disposed on the fixation plate, and are either visible, palpable, measurable on the insert member [15] to readily enable matching for alignment purposes for orientation, and distal positioning for the insert member [15].

Figure 4:
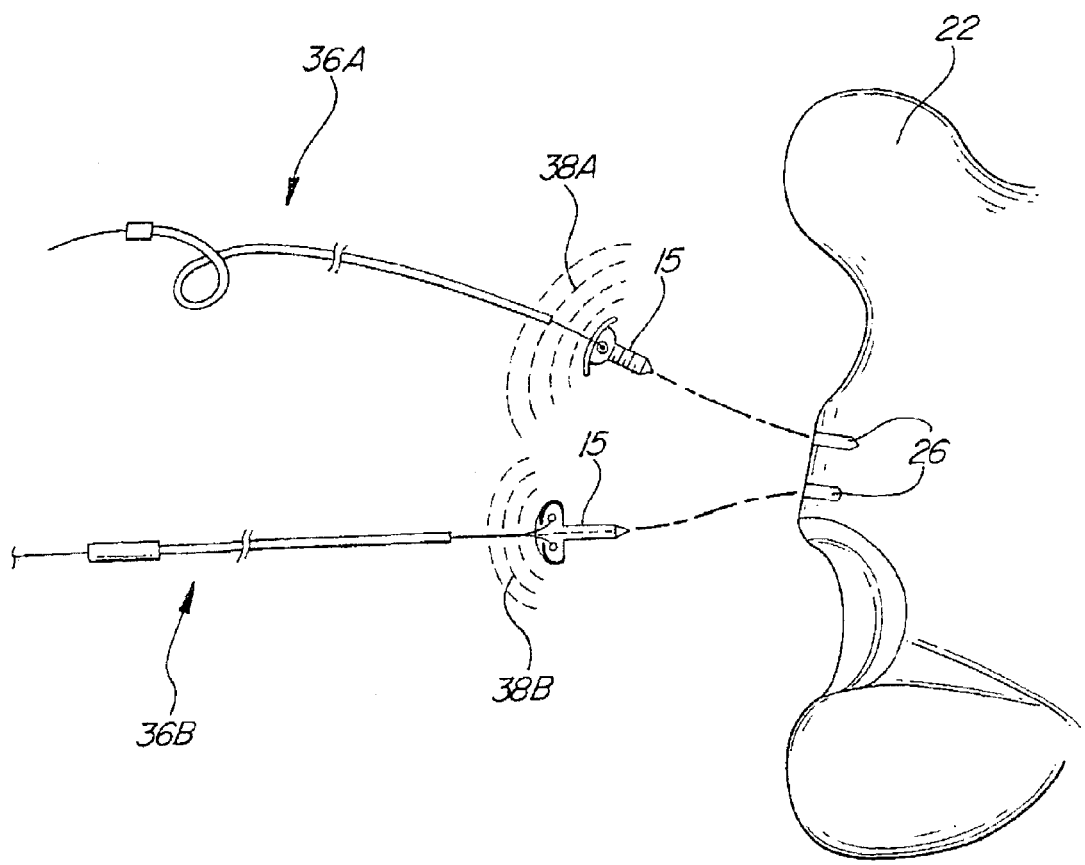
FIG. 4 is an assembly view of another preferred embodiment of a directional-ionizing energy emitting implant device of the present invention, one of the implant devices having an external catheter adaptation and a modified catheter component, the external catheter being implanted at the time of surgery, the external catheter adaptation providing a delivery conduit for placement of the implant device, the modified catheter component having indwelling, activatible energy materials, the modified catheter elongated portion internal channels.

FIG. 4 is an assembly view of another preferred embodiment of an insert compatible implant system of the present invention for use in a hip-socket joint [20], one of the insert members [15] having an external catheter component [36A] and a modified catheter component [36B], the external catheter component [36A] being implanted at the time of surgery, the external catheter component [36A] providing a delivery conduit for placement of the insert member [15], the modified catheter component [36B] having indwelling, activatible energy materials, the modified catheter elongated portion internal channels [31].

An external catheter component [36A] is shown as well as a modified catheter component [36B]. The external catheter component [36A] may be attached at the time of surgery. The catheter may provide either a delivery conduit for permanent or temporary placement of the radio-source materials. In one preferred embodiment, an internal delivery or detachment wire is used to remove a protective shield, or covering, and thereby activate effective energy emissions from a contained source.

Emanating for the cap portion [23] of the insert member [15] in a direction away from the pelvic bone section is the radio energy emission pattern [38A]. The energy source within the insert member [15] is either integral with the insert member [15] or positioned therewithin. The bone port [26] may be drilled, screwed, tapped, hammered, or the like. The bone ports [26] may also be screws that pop out.

In the modified catheter component [36B], a metallic external energy conductive wire feeds into a external catheter wall. The external catheter wall is preferably an insulating polymer carbonate compound. The internal energy conductive source is preferably electrical or electromagnetic. The insert member [15] of the present invention may also be applied with fracture screws, pins, or even plates. Also, other applicable joints include but are not limited to the elbow-arm, shoulder, foot-ankle, and the spine.

Disposed within the cap portion [23] of the inset member of the present invention is a power source—such as an activatible electrical solenoid, an electromagnet, ultrasound-emitting, high frequency crystals, or resistance-type coil. The insert member [15] is preferably constructed of metal alloys or polycarbonate, plastic, or biodegradable materials. Emanating for the cap portion [23] of the insert member [15] in a direction away from the pelvic bone section are energy wave patterns [38B]. Disposed within the elongated portion [24] of the insert member [15] is one or more internal module anchor channels.

Figure 5:
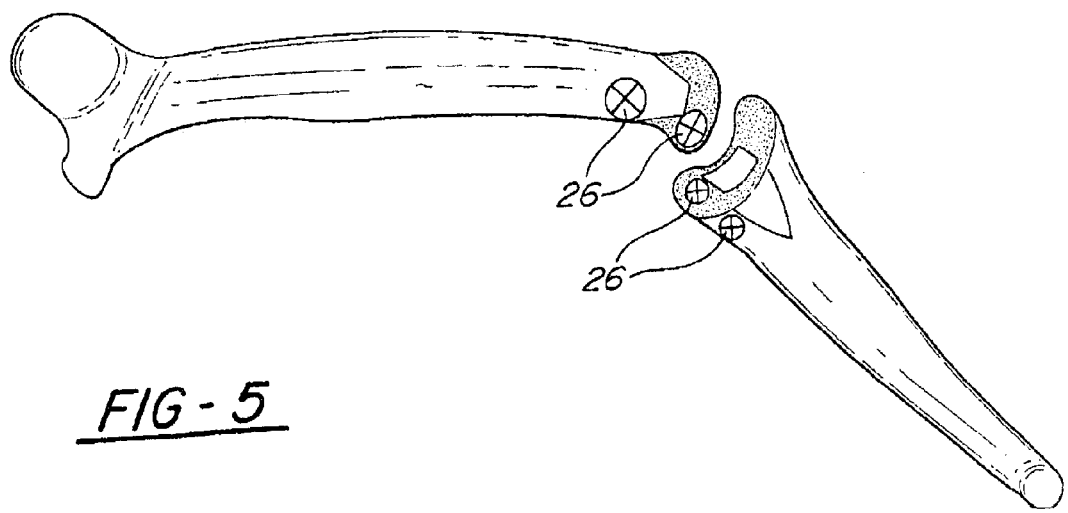
FIG. 5 is an assembly view disclosing a fifth preferred embodiment of a directional-ionizing energy emitting implant device of the present invention, the implant devices being implanted within the femur and tibia, for providing energy from the implant devices to targeted tissue about the knee.

FIG. 5 is an assembly view disclosing a fifth preferred embodiment of the directional-ionizing energy emitting implant or insert member [15] of the present invention, the insert members [15] being implanted within the femur and tibia, for providing directed energy emission from the insert members [15] to targeted tissue about the knee for partial or complete knee prosthesis. As shown, the insert members [15] are compatible with partial and complete knee prosthesis—the knee joint includes tibial plateaus and femoral condyle prosthesis.

There are multiple potential sites for placement of the directional-ionizing energy emitting implant, as for example in a knee joint, to minimize post-surgical delayed scarring, infection, or heterotopic ossification. The insert member [15] of the present invention may be implanted directly for partial or complete prosthesis of other joints, including but not limited to the elbow-arm, shoulder, foot-ankle, and the spine. The insert member [15] of the present invention may be attachable to prosthesis or implant components or separately but dependently placed in bone, cartilage, or soft tissue. Retention can also be achieved with fracture screws, pins, anchors, plates or the like.

There are various design structures and ways of incorporation the radio substance with a prosthetic apparatus, as well as, methods of delivering the radioisotope materials as are hereinafter described.

The therapeutic radiation component is embedded into the prosthetic device prior to in vivo placement; placed in specific sections immediately prior to surgical implantation, placed after satisfactory implantation but prior to wound closure, or injected or cannulated after surgical closure, particularly, if a liquid, gel, or gas is the radio source material. Gels, liquids, gases, or other inter-phase radio compounds can be loaded, injected, molded, screwed, foamed, mixed, taped or by other attachment methods and devices either directly or as a preformed radio-contained or measured unit onto or within a separate leading module specific for the prosthesis device or directly to the prosthetic apparatus, either before, during or after surgical implantation, without the need of an intermediary loading device.

Although this dose range of radiation has been safely used for heterotopic ossification and to minimize infectious processes in such tissue with a negligible risk of delayed tumor formation or tissue necrosis, the prosthesis and femoral head are not exposed to more than a minimal amount of radiation. These are specific sites of desired growth and repair cell migration thereby allowing for stable, permanent integration of the fixed components of the prosthesis into prepped bone. Patients require formal fluoroscopic simulation and dosimetry planning with defined fields for delivery of external beam radiotherapy.

Total doses of less than 700 cGy begin to show diminished efficacy versus compromise for any patient comfort or radiation risks. Accordingly, a dose range of 700 to 900 cGy is able to limit heterotopic ossification formation rates of clinical significance to between 1 and 9 percent.

The radio nuclide component may be any humanly compatible and therapeutically applicable solid, liquid, gas, gel, or other intermediate phase radio nuclide or radioisotope compounds which emit gamma rays, x-rays, beta particles, alpha particles, positrons, auger electrons, photons, or any combination thereof produced by nuclear decay; isomeric transition; electron capture; fluorescent, phosphorescent or luminescent induction; external bombardment activation; electrical stimulation or any combination thereof.

Electrical stimulation includes specifically designed or adoptions of conventional x-ray or electron beam, producing catheters or wires that are placed into or about the module component or radio prosthesis thereby providing a controlled radiation dose to target tissue without necessarily a radioactive component or element.

The separated or attached module can be designed to optimize directional alignment of the electrical-produced, short-distance radiation. In one preferred embodiment of the radio prosthesis device of the present invention, a shielded component is used to minimize effective radiation dose to non-targeted, normal tissue. Such a module may be activated at the time immediately after placement or in delay at recovery or bedside, post-anesthesia. As used herein, "activation" refers to an intended active step taken to expose previously placed radio nuclide containing components, or delayed placement into the modules of a radio nuclide source, or placement via an attached or separated intermediary catheter-type component such that a portal [26] or complete electrical or light radio-decay generated radiation emitting device may be after loaded for a finite period of time.

The integrateable or "free-floating" (but specific in position to the prosthesis) modules or temporary or permanent intermediary catheters (for radioactive source, delivery or removal) may be partial or completely flexible. Various configuration include shapes such as a small spike, loop, half-moon, flat, circular, etc.

The separate modules or attachable intermediary components are biologically safe and dissolved in materials that can intentionally degrade with time after placement in vivo.

In one preferred embodiment of the system of the present invention, the radio nuclide containing component or the radio-directional component, to which an externally delivered or attached radiation producing unit is attached degrades or dissolves in vivo after the radiotherapy dose is administered.

The modules or connectable catheters delivering components may be extracted in vivo, in delayed fashion by an externally remaining string-like attachment, or tabs, reels, or the like, as intentionally placed for clinical administration of radiation to stop heterotopic ossification, infection or inflammatory risk, or excess scar formation by subsequent removal of the modules or catheters after the radiotherapy dose is administered.

Visible markings demarcated as lines, dots, numbers, colors, or a combination of such, with palpable surface changes (such as bumps, rough surfaces or such) are preferably placed upon the radio prosthesis or modules or intermediary interchangeable catheter components in order to facilitate optimal placement, ex vivo or in vivo, in spatial orientation, alignment or matching between each other or the radio nuclide-containing component.

Radio-opaque markers composed of metal, metal alloys, radioactive nuclides or related parent or daughter isotopes, etc. are preferably positioned and fashioned as similar for function and intent as the visible or palpable markers, except that they provide a visible confirmation of the position and orientation of said components by x-ray via fluoroscopy or hard copy x-ray, or equivalent. This can provide measurement assessment and 2-dimensional or 3-dimensional positional identification of the components, as well as confirmatory calculations of expected radiation dose to the adjacent tissue.

In still another preferred embodiment of the radio prosthesis device of the present invention, a magnetic-property-containing element within the independent modules, prosthesis, or associated catheter-type components is directly or separately attached or integrated or impregnated upon the internal or external surfaces. The magnetic field inducing material are preferably made of any known biologically safe heavy metal, metal alloy, or electrically induced magnetic field material (causing field shift of atomic shell electrons) in order to "directionally shift" electron or beta particle radiation toward the targeted tissue or repel similar charged particle energy away from tissue.

Integrated medication, not administered systemically or as an instillation primary therapy, but one whereby an anti-inflammatory or anti-microbial or anti-scar type compound (i.e.—cortico steriod ) is impregnated onto or within any of the components; or may be added to components later, to minimize complications or tissue reactions induced from the device or components themselves (not for general, regional/systemic treatment).

Specific primary radio nuclides, either in stable or radioactive form include but are not limited to xenon, krypton, neon, argon, radon, technetium, rhenium, yttrium, phosphorus, iodine, strontium, samarium, gold, copper, palladium, iridium, tin, rubidium, osmium, platinum, ytterbium, cesium, americium, radium, thallium, chromium, vanadium, barium, titanium, bismuth, and rhodium. More particularly, the specific primary radio nuclides of choice are yttrium, strontium, iridium, iodine, palladium, cesium or technetium.

The utilization and integration of any of these isotopes are applied to the device to enhance individual energy emissions and tissue penetration, in vivo safety, half-life decay properties and specific activities or concentrations of materials. A near ideal effect on the target tissue and depth is thereby achieved with regard to dose rate, depth dose, total does, and elimination rates. The preferred dose rates deliver energy in the range of 50 to 250 cGy/hr. Acceptable dose rates also include from 10 to below 50 cGy/hr and above 250 to 500 cGy/hr. Dose rates in the order of magnitude of from 10 to 200 cGy/min may be of benefit, if the half-life and millicuries of radioactivity can be short (several minutes) and low respectively or radio-material has a short dwell time and is removed. Dose rates per millicurie are between 0.5 cGy/min and 200 cGy/min—mCi.

The total dose delivered to the targeted tissue are preferably between 700 cGy and 2000 cGy. Also, an acceptable total dose is from 200 to below 700 cGy, and above 2000 to 3500 cGy. The total dose to nontargeted soft tissue and bone tissue is less than 500 cGy, but even 500 to 1500 is acceptable. The radio-dose prescription is precalibrated for each specific prosthesis size and application site and marked directly on the prosthesis apparatus. This would be intended to deliver a fixed dose and dose rate range.

Also, a sensor (not shown) may be used to monitor, verify, or control the delivery of the prescribed dose of radiation. Emergency release and retrieval elements enable the immediate removal of at least the radioactive component of the prosthesis.

Other sites of use for a radio-implant include all fixed or mobile joints, compartmental soft tissues and axial or appendicular bones.

Solid or gel-phase compounds may be pre-adhered to the prosthesis by processes involving laser techniques, chemical bonding, electro-ion exchange, thermal conditioning, emulsion-type technologies, or emulsion slip coatings. Ion beam bombardment or deposition to reduce adhesions, thrombus, and provide anti-microbial properties may be applied and is now commercially available from Spire Corp, Bedford, Mass.

Similar methods may be applied to place radio source materials in customized and fitted loading compartments or modules which are attachable at specific sites on the prosthesis and can be placed prior to, during, or after surgical implantation of the prosthetic device.

In addition, a prefabricated, individualized unit dose of radio source material may be constructed in generic or customized form similar to a seed, wire, ball, plaque, powder, pellet, etc. or the like and thereby loaded, with then known specific quantities of radiation upon or within previously described attachable modules, units, compartments and then placed onto or within the prosthetic device. Likewise, these pre-measured, precalibrated radio dose units may be placed directly onto or within the prosthetic apparatus utilizing specifically designed slots, compartments, clips, sections, etc. or the like whereby an intermediary module or loading apparatus is not necessarily required.

The placement of the radio materials may be permanent dwelling, temporary with extraction, or with the option of multiple delayed introductions or retrieval mechanisms.

Primary materials of the individualized radio-unit loading modules or compartments, and prosthetic radio components are made from almost any materials. The radio components preferably comprise plastics; natural or synthetic rubbers; metals; metal-alloys; bio-compatible molecular chain compounds; allogenic or heterogenic natural or synthetic dissoluble compounds when in vivo (natural human, animal, or plant by-product materials); viton rubber; polyurethane, polyethylene, polyimide, polyvinylchloride, polyamide, polytetra fluoroethylene, silicone.

Alternative therapy options for heterotopic ossification include use of non-steroidal anti-inflammatory drugs such as indomethacin, administered at various dosing schedules from 8 days to 6 weeks of treatment. While this method of drug therapy has shown some benefit, it is less effective than a dosage greater than 700 cGy of irradiation for inhibiting clinically significant (Brooker class II–IV) heterotopic ossification. In addition, many patients experience gastrointestinal-intestinal bleeding or gastritis with this drug, requiring additional medications. Furthermore, routine compliance by all at risk patients may falter thereby leaving an unknown risk of eventual heterotopic ossification failure or severity. Both methods offer consideration for optimized, long term outcome.

In yet another preferred embodiment of the implant system of the present invention, the insert member [15] is treated with a bacteriocidal and bacteriostatic material that will kill and prevent the growth of bacteria, viruses, fungi, and the like.

It will be readily apparent to those skilled in the art that the implementation and mechanization of the system and method of the present invention can be varied considerably to improve operation without going beyond the bounds of the present invention. For example, a programmed dose can be applied and administered from an implant that is controlled from an external source, whereby the emission, the decay rate, the initiation, duration, intensity, direction is regulated. In addition, a similar-type device can be mounted on bone tissue and directed at adjacent tissue for treatment, thereby eliminating exposure of healthy tissue to the controlled dose.

Throughout this application, various Patents and Applications are referenced by patent number and inventor. The disclosures of these Patents and Applications in their entireties are hereby incorporated by reference into this specification in order to more fully describe the state of the art to which this invention pertains.

It is evident that many alternatives, modifications, and variations of the directional-ionizing energy-emitting implant of the present invention will be apparent to those skilled in the art in light of the disclosure herein. It is intended that the metes and bounds of the present invention be determined by the appended claims rather than by the language of the above specification, and that all such alternatives, modifications, and variations which form a conjointly cooperative equivalent are intended to be included within the spirit and scope of these claims.

We claim:

1. A surgical procedure comprising: determining a prescribed dosage of ionizing energy that is to be delivered from an insert device to targeted tissue, the targeted tissue having a known ionizing energy-responsive profile, the insert device being positioned within the prosthetic or fixation device, the insert device including an ionizing energy-source material, the ionizing energy-source material in combination with the prosthetic or fixation device defining an actual ionizing energy-delivery distribution field, the ionizing energy-delivery distribution field having a similar configuration to the known ionizing energy-responsive profile of the targeted tissue; introducing the ionizing energy source material into the prosthetic or fixation device; implanting the prosthetic or fixation device into organic tissue during a surgical procedure, the ionizing energy-source material being selected for delivering a predetermined dosage of the ionizing energy from the ionizing energy-source material to targeted tissue, the targeted tissue having a known ionizing energy-responsive profile; activating the ionizing energy-source material once the insert device has been implanted into the organic tissue; and delivering the prescribed dosage of ionizing energy from the ionizing energy-source material to the known ionizing energy-responsive profile of the targeted tissue.

2. The surgical procedure of claim 1, wherein the ionizing energy is selected from a group consisting of luminescent energy, hyperthermic energy, and photo-light energy.

3. A surgical procedure comprising: determining a prescribed dosage of ionizing energy that is to be delivered from an insert device to targeted tissue, the targeted tissue having a known ionizing energy-responsive profile, the insert device being affixed to the prosthetic or fixation device, the insert device including an ionizing energy-source material, the ionizing energy-source material defining an actual ionizing energy-delivery distribution field, the ionizing energy-delivery distribution field having a similar configuration to the known ionizing energy-responsive profile of the targeted tissue; introducing the ionizing energy-source material into the insert device; positioning the insert device into organic tissue during a surgical procedure, the ionizing energy-source material being selected for delivering a predetermined dosage of the ionizing energy from the ionizing energy-source material to targeted tissue, the targeted tissue having a known ionizing energy-responsive profile; activating the ionizing energy-source material once the insert device has been positioned into the organic tissue; and delivering the prescribed dosage of ionizing energy from the ionizing energy-source material to the known ionizing energy-responsive profile of the targeted tissue.

4. The surgical procedure of claim 3, wherein the ionizing energy is selected from a group consisting of luminescent energy, hyperthermic energy, and photo-light energy.

* * * * *